United States Patent [19]
Coleman et al.

[11] Patent Number: 6,090,801
[45] Date of Patent: Jul. 18, 2000

[54] PHARMACEUTICAL COMPOSITIONS CONTAINING CEFTRIAXONE AND PENEMS

[75] Inventors: Kenneth Coleman, Chester Springs, Pa.; Jane Elizabeth Neale, Crawley, United Kingdom

[73] Assignee: SmithKline Beecham p.l.c., Brentford, Germany

[21] Appl. No.: 08/666,282

[22] PCT Filed: Dec. 15, 1994

[86] PCT No.: PCT/EP94/04225

§ 371 Date: Feb. 14, 1997

§ 102(e) Date: Feb. 14, 1997

[87] PCT Pub. No.: WO95/17184

PCT Pub. Date: Jun. 29, 1995

[30] Foreign Application Priority Data

Dec. 23, 1993 [GB] United Kingdom .................... 9326248

[51] Int. Cl.[7] .................. A61K 31/545; A61K 31/53; A61K 31/425; A61K 31/415
[52] U.S. Cl. ................. 514/200; 514/204; 514/206; 514/242; 514/365; 514/369; 514/396
[58] Field of Search ................................. 514/200, 204, 514/206, 242, 365, 369, 396

[56] References Cited

U.S. PATENT DOCUMENTS

| | | | |
|---|---|---|---|
| 4,364,865 | 12/1982 | Ernest et al. | 540/357 |
| 4,629,726 | 12/1986 | Uyeo | 514/195 |
| 5,464,617 | 11/1995 | Bohringer et al. | 424/114 |
| 5,494,666 | 2/1996 | Bohringer et al. | 424/114 |

FOREIGN PATENT DOCUMENTS

94/10178  5/1994  WIPO .

OTHER PUBLICATIONS

Windhols et al., The Merch Index, Tenth Edition, p. 272, abstract No. 1916 (1983).

*Primary Examiner*—Kevin E. Weddington
*Attorney, Agent, or Firm*—Edward R. Gimmi; William T. King; Charles M. Kinzig

[57] ABSTRACT

Pharmaceutical formulations comprising ceftriaxone in combination with a penem of formula (I) in which $R^1$ is hydrogen or an organic group; $R^2$ is a ring system of formula (II), wherein $R^4$ and $R^5$ are hydrogen or one or more substituents; m is 2 or 3; p is 0, 1 or 2; $R^3$ is hydrogen, a pharmaceutically acceptable salt-forming cation or a pharmaceutically acceptable in-vivo hydrolysable ester-forming group; and with a pharmaceutically acceptable carrier. The formulations have antibacterial activity, the compound of formula (I) acting as a β-lactamase inhibitor.

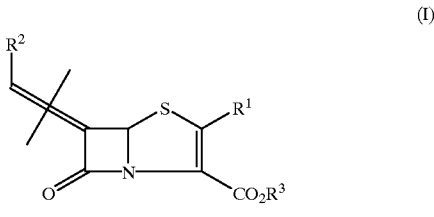

(I)

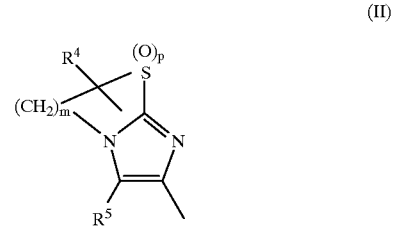

(II)

10 Claims, No Drawings

PHARMACEUTICAL COMPOSITIONS CONTAINING CEFTRIAXONE AND PENEMS

This invention relates to novel antibacterial formulations, in particular to formulations including 6-(substituted-methylene) penems, and derivatives thereof, having β-lactamase inhibitory and antibacterial properties.

The compound ceftriaxone (A):

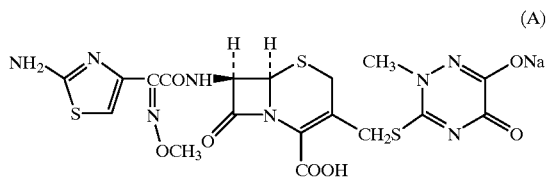

(A)

[6R-[6α,7β(Z)]]-7-[[(2-Amino4-thiazolyl)(methoxyimino)acetyl]amino]-8-oxo-3-[[(1,2,5,6-tetrahydro-2-methyl-5-6-dioxo-1,2,4-triazin-3-yl)thio]-methyl]-5-thia-1-azabicyclo[4-2-O]oct-2-ene-2-carboxylic acid; (6R,7R)-7-[2-(2-amino4-thiazolyl)glyoxylamido]-3-[[2,5dihydro-6-hydroxy-2-methyl-5-oxo-as-triazin-3-yl)thio]methyl]-8-oxo-5-thia-1-azabicyclo[4.2.0]oct-2-ene-2-carboxylic acid $7^2$-(Z)-(O-methyloxime) is a known antibiotic compound. The term "ceftriaxone" as used herein includes all pharmaceutically acceptable derivatives thereof, including pharmaceutically acceptable salts and in-vivo hydrolysable esters. Although widely used it suffers the general problems of all cephalosporins in being less effective against anaerobes, and of generally rapid development of β-lactamase mediated resistance by microorganisms.

To overcome the problem of lack of activity against anaerobes, ceftriaxone may be administered in combination with metronidazole. Recently, the activity of ceftriaxone against anaerobes such as *Bacteroides fragilis* has been reported to be enhanced by coadministration with the β-lactamase inhibitor tazobactam (J. Antimicrobial Chemotherapy (1993), 32, 307–312). This combination suffers from a potential problem, however, because of the marked disparity in the serum half-lives of ceftriaxone (ca. 8 hours) and tazobactam (ca. 1 hour).

According to the present invention a pharmaceutical formulation comprises ceftriaxone in combination with a penem of formula (I):

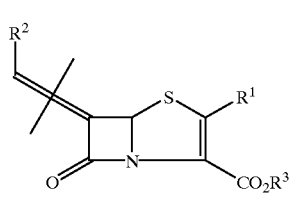

(I)

in which:

$R^1$ is hydrogen or an organic substituent group;

$R^2$ is a fused bicyclic heterocyclic ring system of general formula:

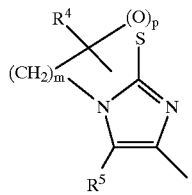

wherein $R^4$ and $R^5$ are independently hydrogen or one or more substituents replacing hydrogen atoms in tile ring system shown; m is 2 or 3; p is zero, 1 or 2; and $R^3$ is hydrogen, a pharmaceutically acceptable salt-forming cation or a pharmaceutically acceptable in-vivo hydrolysable ester-formig group; and the symbol =/= indicates that the double bond may be in either the E or Z configuration; and with a pharmaceutically acceptable carrier.

The compound of formula (I), its salts and esters, may exist in a number of isomeric forms, all of which, including racemic and diastereoisomeric formns are encompassed within the formulations of thle present invention.

The compounds of formula (I) may exist in two isomeric forms at the methylene group at thle 8-position, ie the E- and Z- isomeric forms. The Z-isomer is generally preferred as generally being the more active form.

Preferred forms of the compounds of formula (I) have the structure (IA):

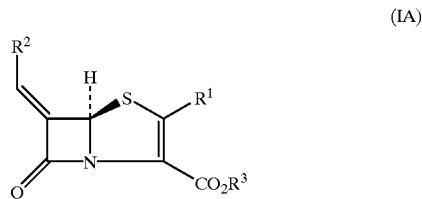

(IA)

In general formula (I), $R^1$ denotes hydrogen (which is preferred) or an organic group, which may suitably be linked to the penem ring system through a sulphur or carbon atom. For example, $R^1$ may represent hydrogen or a group of formula —$R^5$ or —$SR^5$, where $R^5$ denotes an unsubstituted or substituted ($C_{1-10}$) hydrocarbon or heterocyclyl group.

Preferably, $R^1$ represents hydrogen, ($C_{1-10}$)alkyl or ($C_{1-10}$)alkylthio, or substituted ($C_{1-10}$)alkyl or substituted ($C_{1-10}$)-alkylthio, wherein the substituent may be hydroxy, ($C_{1-6}$)alkoxy, ($C_{1-6}$)allanoyloxy; halogen, mercapto, ($C_{1-6}$) alkylthio, heterocyclylthio, amino, (mono or di)-($C_{1-6}$) alkylamino, ($C_{1-6}$)alkanoylamino, carboxy, or ($C_{1-6}$) alkoxycarbonyl.

Examples of suitable organic groups $R^1$ include methyl, ethyl, propyl, methylthio, ethylthio, methylsulphinyl, ethylsulphinyl, hydroxymethyl, methoxy-methyl, ethoxymethyl, acetoxymethyl, (1 or 2)-acetoxyethyl, aminomethyl, 2-aminoethyl, acetamidomethyl, 2-acetamidoethyl, carboxymethyl, 2-hydroxy-ethylthio, methoxymethylthio, 2-methoxyethylthio, acetoxymethylthio, 2-amino-ethylthio, acetamidomethylthio, 2-acetamidoethylthio, carboxymethylthio, 2-carboxyethylthio, aryl (especially phenyl), arylthio (especially phenylthio), pyridyl, pyrimidyl, isoxazolyl, pyrimidylthio, tetrazolylthio, and pyridylthio groups.

In particular, $R^1$ may be hydrogen.

Suitable groups $R^2$ include: 2,3-dihydroimidazo[2,1-b]thiazol-6-yl, 2,3-dihydro-1-(R,S)-oxoimidazo[2, 1-b]

thiazol-6-yl, 2,3-dihydro-1,1-dioxoimidazo[2,1-b]thiazol-6-yl, 6,7-dihydro-5H-imidazo[2,1-b]-thiazin-2-yl and 6,7-dihydro-8,8-dioxo-5H-imidazo[2,1-b][1,3]thiazin-2-yl.

Examples of suitable substituents $R^4$ and $R^5$ include $(C_{1-6})$alkanoyl, $(C_{1-6})$alkanoyloxy, heterocyclyl, amino, $(C1-6)$alkanoylamino, (mono or di)-$(C_{1-6})$alkylamino, hydroxy, $(C_{1-6})$alkoxy, sulpho, mercapto, $(C_{1-6})$alkylthio, $(C_{1-6})$alkylsulphinyl, $(C_{1-6})$alkyl-sulphonyl, heterocyclylthio, arylthio, sulphamoyl, carbamoyl, amidino, guanidino, nitro, halogen, carboxy, carboxy salts, carboxy esters, arylcarbonyl, and heterocyclylcarbonyl groups, and also unsubstituted or substituted $(C_{1-6})$alkyl, $(C_{2-6})$alkenyl, $(C_{2-6})$alkynyl, aryl, and aryl$(C_{1-6})$aLkyl groups.

Examples of suitable optional substituents for the above-mentioned $(C_{1-6})$alkyl, $(C_{2-6})$alkenyl, $(C_{2-6})$alkynyl, aryl and aryl$(C_{1-6})$alkyl substitutents include $(C_{1-6})$alkanoyl, $(C_{1-6})$alkanoyloxy, heterocyclyl, amino, $(C_{1-6})$alkanoylamino, (mono or di)-$(C_{1-6})$alkylamino, hydroxy, $(C_{1-6})$alkylsulphinyl, $(C_{1-6})$alkyl-sulphonyl, heterocyclylthio, arylthio, sulphamoyl, carbamoyl, amidino, guanidino, nitro, halogen, carboxy, carboxy salts, carboxy esters,arylcarbonyl and heterocyclylcarbonyl groups.

Suitably $R^4$ and $R^5$ may both be hydrogen.

Suitable pharmaceutically acceptable salts of the 3-carboxylic acid group of ceftriaxone or the compound of formula (I) or of other carboxylic acid groups which may be present as optional substituents include those with a metal, e.g those in which $R^3$ is a metal ion e.g. aluminium salts, alkali metal salts (e.g. sodium, lithium or potassium salts), alkaline earth metal salts (e.g. calcium or magnesium salts), ammonium salts, and substituted ammonium salts, for example those with lower alkylamines (e.g.triethylamime), hydroxy-lower alkylamines (e.g. 2-hydroxyethylamiie), di(2-hydroxyethyl)amine tri(2-hydroxyethyl)amine), bis-(2-hydroxyethyl)amine, tris-(2-hydroxyethyl)amine, lower-alkylamines (e.g. dicyclohexyl-amine), or with procaine, dibenzylamine, N,N-dibenzyl-ethylenediamine, 1-ephenamine, N-methylmorpholine, N-ethylpiperidine, N-benzyl-β-phenethylamine, dehydroabietylamine, ethylenediamine, N,N'-bishydroabietylethylenediamine, bases of the pyridine type (e.g. pyridine, collidine and quinoline), and other amines which have been or can be used to form quaternary ammonium salts with penicillins.

Pharmaceutically acceptable salts may also be acid addition salts of any amino or substituted amino group(s) that may be present as optional substituents on ceftriaxone or the compound of formula (I), or of any heterocyclic group ring nitrogen atoms. Suitable salts include for example hydrochlorides, sulphates, hydrogen sulphates, acetates, phosphates etc. and other pharmaceutically acceptable salts will be apparent to those skilled in the art. Suitable addition salts are the hydrochlorides and hydrogen sulphates.

Preferred salts are those in which $R^3$ is sodium.

Examples of suitable pharmaceutically acceptable in vivo hydrolysable ester groups which $R^3$ may suitably comprise include those which break down readily in the human body to leave the parent acid or its salt. Suitable ester groups of this type include those of part formulae (i), (ii), (iii), (iv) and (v):

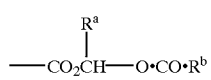
(i)

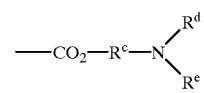
(ii)

(iii)

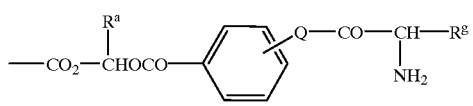
(iv)

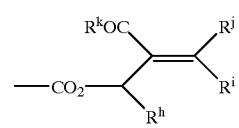
(v)

wherein $R^a$ is hydrogen, $(C_{1-6})$ alkyl, $(C_{3-7})$ cycloalkyl, methyl, or phenyl, $R^b$ is $(C_{1-6})$ allyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$(C_{1-6}$ alkyl) amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted-by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$(C_{1-6})$alkoxy or aryl.

Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxy-alkyl groups, such as ethoxycarbonyloxymethyl, α-ethoxycarbonyloxyethyl and propoxycarbonyl-oxyethyl; dialkylaminoalkyl especially di-loweralkylamino alkyl groups such as dimethylaminomethyl, dimethylaminoethyl, diethylaminomethyl or diethylamino-ethyl; 2-(alkoxycarbonyl)-2-alkenyl groups such as 2-(isobutoxycarbonyl)pent-2-enyl and 2-(ethoxycarbonyl) but-2-enyl; lactone groups such as phthalidyl and dimethox-yphthalidyl; and esters linked to a second β-lactam antibiotic or to a β-lactamase inhibitor.

A further suitable pharmaceutically acceptable in vivo hydrolysable ester group is that of the formula:

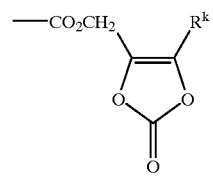

wherein $R^k$ is hydrogen, $C_{1-6}$ allyl or phenyl.

When used herein the term 'aryl' includes, preferably denotes, phenyl and naphthyl, each optionally substituted with up to five, preferably up to three, groups selected from halogen, mercapto, ($C_{1-6}$) alkyl, phenyl, ($C_{1-6}$) alkoxy, hydroxy($C_{1-6}$)alkyl, mercapto($C_{1-6}$)alkyl, halo($C_{1-6}$) alkyl, hydroxy, amino, nitro, carboxy, ($C_{1-6}$) alkylcarbonyloxy, alkoxycarbonyl, formyl, or ($C_{1-6}$) alkylcarbonyl groups.

The terms 'heterocyclyl' and 'heterocyclic' as used herein include aromatic and non-aromatic, single and fused, rings suitably containing up to four hetero-atoms in each ring selected from oxygen, nitrogen and sulphur, which rings may be unsubstituted or substituted by, for example, up to three groups selected from halogen, ($C_{1-6}$)alkyl, ($C_{1-6}$) alkoxy, halo($C_{1-6}$)alkyl, hydroxy, carboxy, carboxy salts, carboxy esters such as ($C_{1-6}$)alkoxycarbonyl, ($C_{1-6}$) alkoxycarbonyl($C_{1-6}$)alkyl, aryl, and oxo groups. Each heterocyclic ring suitably has from 4 to 7, preferably 5 or 6, ring atoms. The term 'heteroaryl' refers to heteroaromatic heterocyclic ring or ring system, suitably havmg 5 or 6 ring atoms in each ring. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

When used herein the terms 'alkyl', 'alkenyl', 'nyl' and 'alkoxy' include straight and branched chain groups containing from 1 to 6 carbon atoms, such as methyl, ethyl, propyl and butyl. A particular alkyl group is methyl.

When used herein the term 'halogen' refers to fluorine, chlorine, bromine and iodine.

It will be appreciated that also included within the scope of the formulations of this invention are formulations which include salts and carboxy-protected derivatives, including in vivo hydrolysable esters, of any carboxy groups that may be present as optional substituents in ceftriaxone or in compounds of formula (I).

Certain compounds of formula (I) may include an amino group which may be protected. Suitable amino protecting groups are those well known in the art which may be removed under conventional conditions if required without disruption of the remainder of the molecule.

Examples of amino protecting groups include ($C_{1-6}$) alkanoyl; benzoyl; benzyl optionally substituted in the phenyl ring by one or two substituents selected from ($C_{1-4}$) alkyl, ($C_{1-4}$) alkoxy, trifluoromethyl, halogen, or nitro; ($C_{1-4}$) alkoxycarbonyl; benzyloxycarbonyl or trityl substituted as for benzyl above; allyloxycarbonyl, trichloroethoxycarbonyl or chloroacetyl.

Some compounds of formula (I) and (IA) may be crystallised or recrystallised from solvents such as organic solvents. In such cases solvates may be formed. This invention includes within its scope formulations which employ stoichiometric solvates of ceflriaxone or compounds of Formula (I) including hydrates as well as compounds containing variable amounts of solvents such as water that may be produced by processes such as lyophilisation.

Since the compounds of formula (I) and (IA) are β-lactamase inhibitors and/or antibiotics and are intended for-use in pharmaceutical compositions it will readily be understood that they are preferably each used in substantially pure form, for example at least 60% pure, more suitably at least 75% pure and preferably at least 85% pure, especially at least 95% pure particularly at least 98% pure (% are on a weight for weight basis). Impure preparations of the compounds may be used for preparing the more pure forms used in the pharmaceutical formulations; these less pure preparations of the compounds should contain at least 1 %, more suitably at least 5% and preferably from 10 to 59% of a compound of the formula (I) or (IA) or ester or salt thereof.

Specific compounds of formula (I) suitable for use in the formulations of this invention include the following pharmaceutically acceptable salts:

Sodium (5R)-6-[(Z)-(2,3-dihydroimidazo [2,1-b] thiazol-6-yl) methylene]-penem-3-carboxylate, which is a preferred compound of Formula (I).

Sodium (5R)-6-[(Z-(2,3-dihydro-1(R,S)-oxoimidazo [2,1-b] thiazol-6-5yl)methylene]penem-3-carboxylate.

Sodium (5R)-6-[(Z-(2,3-dihydro-1,1-dioxoimidazo [2,1-b]thiazol-6-yl)methylene]penem-3-carboxylate.

Sodium (5R)-6-[(Z)-(6,7-dihydro-5H-imidazo [2,1-b][1,3] thiazin-2-yl)methylene]penem-3-carboxylate.

Sodium (5R)-6-[(Z)-(6,7-dihydro-8,8-dioxo-5H-imidazo [2,1-b][1,3]thiazin-2-yl)methylene] penem-3-carboxylate.

Compounds of formula (I) as defined above, including the above-mentioned specific and preferred compounds and their methods of preparation, are disclosed in WO 94/10178 (PCT/EP 93102894 published 11 May 1994).

The compounds of formula (I) have β-lactamase inhibitory and antibacterial properties. The combination of ceftriaxone with one or more compounds of formula (I) in this invention significantly enhances the susceptibility of organisms having a β-lactamase medicated resistance mechanism, e.g. *Enterobacter spp., Klebsielia spp* and *Escherichia spp* to ceftriaxone. Moreover the combination significantly enhances the effectiveness of ceftriaxone against *Bacteroides spp.* e.g. *Bacteroides fragilis.* Also some compounds of formula (1), for example sodium (SR)-6-[(Z)-(2,3-dihydroimidazo [2,1-b] thiazol-6yl) methylene]penem-3-carboxylate, appear to have a serum half life of a length more compatible with ceftriaxone.

The formulations of the invention are useful for the treatment of infections e.g. by such microorganism in animals, especially mammals, including humans, in particular in humans and domesticated (including farm) animals. The compounds may be used, for example, for the treatment of infections of, inter alia the respiratory tract, the urinary tract, and soft tissues, especially in humans.

The formulations may be used for the treatment of infections caused by strains of, for example, *Enterobacter spp.* e.g. *Enterobacter cloacae, Staphylococcus aureus, Klebsiella aerogenes, Escherichia coli, Proteus sp.,* and *Bacteroides fragilis.* The compound of formula (I) or (IA) and ceftriaxone can be administered separately or in the form of a single composition containing both active ingredients as discussed in more detail below. The compositions of the invention include those in a form adapted for oral, topical or parenteral use and may be used for the treatment of bacterial infection in mammals including humans. The compounds of formula (I), and ceftriaxone are particularly suitable for parenteral administration.

Ceftriaxone and the compound(s) of formula (I) or (IA) may be formulated for administration in any convenient way for use in human or veterinary medicine, by analogy with other antibiotic formulations. Ceftriaxone and the compound (s) of formula (I) may be formulated for administration by any route, such as oral or topical, but particularly by parenteral administration. The formulations may be in the form of liquid preparations, such as sterile solutions or suspensions for parenteral administration, or in a dry or concentrated form for make up into such a liquid preparation.

For parenteral administration, fluid unit dosage forms may be prepared utilizing ceftriaxone and the compound(s)

of formula (I) in combination, and a carrier which is a sterile vehicle, water being preferred. The ceftriaxone and the compound(s) of formula (I), can, depending on the vehicle and concentration used, be either suspended or dissolved in the vehicle. In preparing solutions the ceftriaxone and the compound(s) of formula (I) can be dissolved in water for injection and filter sterilised before filling into a suitable vial or ampoule and sealing. The compound(s) of formula (I) and ceftriaxone may be made up separately in respective fluid vehicles, or may be made up mixed, in the same fluid vehicle, or described above.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The ceftriaxone and the compound(s) of formula (I) can be sterilised by exposure to ethylene oxide before suspending in the sterile vehicle. Advantageously, a surfactant or wetting agent is included in the composition to facilitate uniform distribution of the compound.

Ceftriaxone may be administered to the patient with a synergistically effective amount of one or more compound(s) of formula (I) or (IA).

The compound(s) of formula (I) or (IA) may suitably be administered to the patient in the formulations of this invention at a daily dosage of from 0.7 to 50 mg/kg of body weight. For an adult human (of approximately 70 kg body weight), from 50 to 3000 mg, preferably from 100 to 1000 mg, of a compound according to the invention may be adminstered daily, suitably in from 1 to 6, preferably from 2 to 4, separate doses. Higher or lower dosages may, however, be used in accordance with clinical practice.

Ceftriaxone may be administered to the patient at a daily dosage corresponding to the dosage in which it is presently used alone, for example up to 2000 mg daily depending upon the severity of the infection, for example 1000 mg or 2000 mg once daily.

When the compositions according to the invention are presented in unit dosage form, each unit dose may suitably comprise from 25 to 1000 mg, preferably from 50 to 500 mg, of one or more compounds of formula (I). Each unit dose may, for example, be 62.5, 100, 125, 150, 200 or 250 mg of a compound of formula (I). Unit doses may include amounts of ceftriaxone up to and including amounts corresponding to those in which ceftriaxone is currently administered in unit doses, e.g. up to 1000–2000 mg per unit dose.

The ratio of the amount of the compound(s) of formula (I): ceftriaxone may vary within a wide range. The said ratio may, for example, be from 1:1 to 1:100; more particularly it may for example, be from 1:1 to 1:30, typically 1:1 to 1:12. A suitable ratio appears to be around 1:4.

In a particular embodiment the present invention provides a pharmaceutical formulation comprising ceftriaxone in combination with sodium (5R)-6-[(Z)-(2,3-dihydroimidazo [2,1-b] thiazol-6-yl) methylene]penem-3-carboxylate.

The present invention also provides a method for the preparation of a pharmaceutical formulation comprising ceftriaxone and a compound of formula (I), which method comprises admixing the combination of the compound of formula (I) and ceftriaxone and a pharmaceutically acceptable carrier.

The present invention provides ceftriaxone in combination with a compound of formula (I), for use as a therapeutic agent.

The present invention further provides ceftriaxone in combination with a compound of formula (I), for use in the treatment of bacterial infections.

The present invention also includes a method of treating bacterial infections in humans and animals which comprises the administration of a therapeutically effective amount of ceftriaxone in combination with a compound of formula (I).

The present invention also includes a method of enhancing the antibacterial effectiveness of ceftriaxone, comprising combining ceftriaxone with a compound of formula (I). In this method the enhancement is generally by inhibition of the bacterial β-lactamase enzymes which impart resistance to ceftriaxone.

The present invention also includes the use of ceftriaxone in combination with a compound of formula (I), in the manufacture of a medicament for the treatment of bacterial infections.

The following examples illustrate the antibacterial effectiveness of the combination of compounds of formula (I) with ceftriaxone, and the enhancement of the antibacterial activity of ceftriaxone by compounds of formula (I).

EXAMPLE 1.

MIC data in μg/ml of ceftriaxone against various microorganisms, both alone and in combination with the compound of formula (I) Sodium (5R)-6-[(Z)-(2,3-dihydroimidazo [2,1-b] thiazol-6-yl) methylene]penem-3-carboxylate prepared according to Example 1 of WO 94/10178, are given below:

| Organism | MIC Ceftriaxone alone | MIC + 1 μg/1 ml of compound of Formula (I) |
|---|---|---|
| *Klebsiella pneumoniae* 4 | 16 | 0.5 |
| *Enterobacter cloacae* P99 | 128 | 0.5 |
| *Bacteroides fragilis* VP1 8908 | 128 | 2 |

This MIC data indicates the substantial enhancement of antibacterial activity of ceftriaxone resulting from the b-lactamase inhibitory effect of the compound of formula (I).

What is claimed is:

1. A pharmaceutical formulation comprising ceftriaxone in combination with a penem of formula (I):

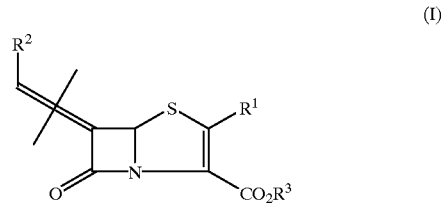

in which:

$R^1$ is hydrogen or an organic substituent group;

$R^2$ is a fused bicyclic heterocyclic ring system of general formula:

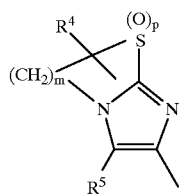

wherein $R^4$ and $R^5$ are independently hydrogen or one or more substituents replacing hydrogen atoms in the ring system shown; m is 2 or 3; p is zero, 1 or 2; and $R^3$ is hydrogen, a salt-forming cation or an ester-forming group; and the symbol =/= indicates that the double bond may be in either the E or Z configuration; and with a pharmaceutically acceptable carrier.

2. A formulation according to claim 1 wherein the compound of formula (I) has the structure (IA):

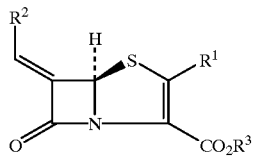

(IA)

wherein $R^1$, $R^2$ and $R^3$ are as described in claim 1.

3. A formulation according to claim 2 wherein the compound of formula (I) is sodium (5R)-6-[(Z)-(2,3-dihydroimidazo [2,1-b] thiazol-6-yl) methylene]penem-3-carboxylate.

4. A formulation according to claim 1 formulated for parenteral administration.

5. Formulation according to an claim 1 when presented in unit dosage form, each unit dosage form comprising from 25 to 1000 mg of one or more compounds of formula (I) and up to 2000 mg of ceftriaxone.

6. A formulation according to claim 1 comprising a ratio of the amount of the compound(s) of formula (I): ceftriaxone within the range from 1:1 to 1:100.

7. A formulation according to claim 6 wherein the ratio of the amount of the compound(s) of formula (I): ceftriaxone is around 1:4.

8. A method for the preparation of a pharmaceutical formulation comprising ceftriaxone and one or more compound(s) of formula (I), comprising admixing the combination of the compound(s) of formula (I) and ceftriaxone and a pharmaceutically acceptable carrier.

9. A method of treating bacterial infections in humans and animals which comprises the separate or combined administration of a therapeutically effective amount of ceftriaxone with a compound of formula (I).

10. A method of enhancing the antibacterial effectiveness of ceftriaxone, comprising separate or combined administration of ceftriaxone with a compound of formula (I).

* * * * *